United States Patent [19]  
Lin et al.

[11] Patent Number: 4,797,455  
[45] Date of Patent: Jan. 10, 1989

[54] ISOCYANATES BLOCKED WITH 1-AMINO-ALKYLIMIDAZOLES AS EPOXY CURING AGENTS

[75] Inventors: Shiow-Ching Lin, Ellicott City; Ping-Lin Kuo, Columbia, both of Md.

[73] Assignee: W. R. Grace & Co.-Conn., New York, N.Y.

[21] Appl. No.: 82,168

[22] Filed: Aug. 6, 1987

[51] Int. Cl.$^4$ ............................................. C08G 59/40
[52] U.S. Cl. ..................................... 525/504; 528/45; 528/94; 528/117
[58] Field of Search ........................... 528/45; 525/504

[56] References Cited

U.S. PATENT DOCUMENTS

| | | | |
|---|---|---|---|
| 4,041,019 | 8/1977 | McGraw et al. | 548/301 |
| 4,335,228 | 6/1982 | Beitchman et al. | 525/528 |
| 4,533,715 | 8/1985 | Lee et al. | 528/45 |

FOREIGN PATENT DOCUMENTS 0024119  2/1981  European Pat. Off.

OTHER PUBLICATIONS

Chem. Abs. 78, 592299t, Bull et al., Curable Epoxy, etc. (1973).
Chem. Abs. 83, 180415j, Harrison et al., Hardening Epoxy, etc., (1975).
Chem. Abs. 85, 78946n, Doorakian et al., Epoxy Resin, etc. (1976).
Chem. Abs. 94, 48349p, Moser et al., Storable, Homog., etc. (1981).
Chem. Abs. 102, 25735f, Nitro El. Ind., Epoxy Resin, etc. (1985).
Chem. Abs. 102, 26023j, Toho Co., Epoxy Resin Comps. (1985).
Ricciardi et al., Mechanism of Imidazole Catalysis, etc., J. Pol. Sci.: Pol. Let. Ed., 20, 127–133 (1982).
Ricciardi et al., Mechanism of Imidazole Catalysis, etc., J. Pol. Sci.: Pol. Chem. Ed., 21, 1475–1490 (1983).

*Primary Examiner*—John Kight
*Assistant Examiner*—Frederick F. Krass
*Attorney, Agent, or Firm*—Charles A. Cross; Richard P. Plunkett

[57] ABSTRACT

Novel curing agents for heat-curable single package epoxy resins, the agents being adducts of aminoalkyl imidazoles with isocyanates. Cures are effected on heating the epoxy resin for times as short as 5 seconds.

16 Claims, No Drawings

ISOCYANATES BLOCKED WITH 1-AMINO-ALKYLIMIDAZOLES AS EPOXY CURING AGENTS

RELATED APPLICATION

USSN 082,179 filed Aug. 6, 1987, "Aminopropylimidazoles," inventors Shiow-Ching Lin and Jennifer M. Quirk, discloses and claims the hydrogenation of 1-cyanoethylimidazoles to make the corresponding aminopropyl derivatives.

FIELD OF THE INVENTION

This invention relates to single package heat-curable epoxy resin systems, and more specifically to novel accelerators/curing agents for such systems.

BACKGROUND OF THE INVENTION AND PRIOR ART

Single package epoxy resin systems conventionally include a latent curing agent, typically dicyandiamide. This curing agent requires a long cure period, even at high temperatures. For example, it can be demonstrated from differential scanning calorimetric studies that the dicyandiamide-epoxy system (e.g., Epon 828, Shell Chemical Company), without the presence of an accelerator, exhibits an onset cure temperature at 193° C. Normally such mixture has to be cured above 180° C. for at least 30 minutes to obtain a cured thermoset for practical applications (adhesives, coatings, and sealants). To increase the curing speed and to reduce the curing temperature, curing accelerators such as imidazoles and ureas have been incorporated into epoxy-dicyandiamide systems. Due to the basic nature of imidazoles, the prepared one-package thermosetting materials normally run into storage stability problems.

(Note: "Onset cure temperature" is a term peculiar to the thermoset resin art. Consider the curing curve. The curve is substantially flat (base line) until the resin reaches a temperature at which curing begins. Then the curve slopes sharply upward, as a measure of the amount of curing that has taken place. "Onset cure temperature" is the intersection of tangents drawn respectively to the base line and to the sharp upward curve. A consideration of the geometry of the curing curve and this intersection will show that curing occurs before onset cure temperature is reached.)

Various urea derivatives have been reported as epoxy accelerators, with and without dicyandiamide, e.g. (all references are to Chemical Abstracts):

N-phenyl-N',N'-dimethyl urea; 78(10):59299t.
Phenylurea or 1,3-diphenylurea; 83(22):180415j.
Substituted urea or thiourea; 85(12):78946n.
Substituted urea (Monuron); 94(8):48349p.
3-(substituted phenyl)-1,1-dimethylurea; 102(4):-25735f and 102(4):26023j.

In other attempts to hasten the cure of epoxy-dicyandiamide systems, certain imidazole-isocyanate reaction products have been tried. European patent application 024,119 of July 21, 1980 describes a succinic acid salt of imidazole modified by phenylisocyanate which when combined with an epoxy resin of polyglycidyl ether, has a shelf life of only 2-3 days. U.S. Pat. No. 4,335,228 describes certain isocyanate blocked imidazoles with excellent shelf life, but which are useful only with epoxy resins that are solid at room temperature, a requirement that rules out use with some of the most useful epoxies. The accelerator claimed in U.S. Pat. No. 4,533,715 is naphthyldiisocyanate blocked with imidazole or certain imidazole derivatives. Shelf life of 6-8 months is claimed, along with cure times of 5 minutes at 250° F. (with Epon 828). In U.S. Pat. No. Pat. No. 4,041,019 the epoxy curing agent is an imidazole capped with an isocyanate.

The instant invention concerns a novel class of imidazole compounds that serve as curing agents as well as curing accelerators for single-package epoxy thermosetting systems. The invention deals with the preparation and the application of these novel imidazoles for curing epoxy resins at an extremely rapid speed and at a reduced cure temperature without affecting the storage stability of the mixture of epoxy resin plus imidazole compound. Details are given below.

The Invention

Our epoxy accelerator/curing agents are a new class of compounds, $$X_mY \quad (I)$$

where
X is

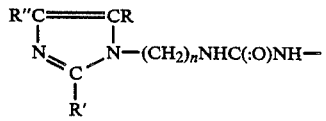

m has a value of at least 1 and is preferably 1-3;
R and R" are independently H, methyl, or ethyl;
n is 2-5;
R' is methyl or ethyl; and
Y has valence m and is an organic radical.

The aforesaid new compounds are made by reacting an imidazole of the formula

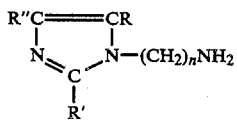

with an isocyanate of the formula $$(III) \ Y(NCO)_m \quad (III)$$

where m, n, R, R', R", and Y have the values above given.

Within (II), 1-aminoethyl-2-methyl imidazole is a known compound. See use in Example 1.

The aminopropylimidazoles in (II) are believed novel, e.g., 1-aminopropyl-2-ethyl-4-methyl imidazole, as made in Example 6 and used in Example 5.

In general, the compounds in (I) can be readily synthesized by the reaction of an amino-imidazole, such as 1-aminoethyl-2-methyl imidazole, with an isocyanate, such as toluenediisocyanate. The isocyanate can be mono- or multi-functional. The resulting products have the structure set forth in (I).

It will be noted that the compounds in (I) contain complete urea and complete imidazole functional groups, i.e., all urea nitrogen is derived from aminoalkyl, not (as in the adducts in the aforesaid European patent application 24,119, U.S. Pat. No. 4,335,228, 4,041,019, 4,533,715) from imidazole nitrogen. The structural difference appears minor, but it results in a surprising improvement in cure times.

A wide variety of isocyanates is useful in the invention, viz.:

Monoisocyanates such as methyl isocyanate, propyl isocyanate, isopropyl isocyanate, n-butyl isocyanate, cyclohexyl isocyanate, octadecyl isocyanate, phenyl isocyanate, p-chlorophenyl isocyanate, and 3,4-dichlorophenyl isocyanate.

Diisocyanates such as hexamethylene diisocyanate, m-phenylene diisocyanate, 2,4-toluene diisocyanate, 4,4'-diphenylmethane diisocyanate, dianisidine diisocyanate, tolidine isocyanate, isophorone diisocyanate, 4,4'-dicyclohexylmethane, chlorophenylene-2,4-diisocyanate, 1,5-naphthalene diisocyanate, ethylene diisocyanate, diethylidene diisocyanate, propylene-1,2-diisocyanate, cyclohexylene-1,2-diisocyanate, 3,3'-dimethyl-4,4'-biphenylene diisocyanate, 3,3'-dimethoxy-4,4'-bipheylene diisocyanate, 3,3'-dimethoxy-4,4'-biphenylene diisocyanate, 3,3'-diphenyl-4,4'-biphenylene diisocyanate, 4,4'-biphenylene diisocyanate, 3,3'-dichloro-4,4'-biphenylene diisocyanate, and furfurylidene diisocyanate.

Triisocyanates such as biuret of hexamethylene diisocyanate and triphenylmethane triisocyanate.

Polyisocyanates such as polymeric diphenylmethane diisocyanate.

The epoxy resins to which our accelerator is applicable include those conventionally available. They are those using conventional reactants, e.g., as halohydrins: epichlorohydrin, dichlorohydrin, 1,2-dichloro-3-hydroxypropane, etc. As diepoxies, butadiene dioxide, diglycidyl ether, etc. As mononuclear di- and trihydroxy phenols, resorcinol, hydroquinone, pyrocatechol, saligenin, phloroglucinol, etc. As polynuclear polyhydroxy phenols, Bisphenol A, Bisphenol F, trihydroxyl diphenyl dimethyl methane, 4,4'-dihydroxy biphenyl, dihydroxyl diphenyl sulfone, etc.

As is well known, epoxy resins are in resin form both before and after being cured, and many (though not all) are initially in liquid form. The curing process cross-links the starting resin. When curing is by heating (as is the general practice in industry), the effect is thus a thermosetting operation. Our invention, as noted, is limited to heat-curing and to heat-curable epoxy resins.

An outstanding advantage of our new compositions is that they combine the functions of accelerator and curing agent. This means that conventional curing agents such as dicyandiamide may be omitted from the epoxy resin. On the other hand epoxies that contain dicyandiamide will not be adversely affected by the use of our accelerator/curatives. Besides (in the typical case) effecting cure in seconds, our materials are storage stable. (After 30 days in storage no significant change is detectable.)

The epoxy resin may be modified by polyols, polyesters, rubber, and the like.

The epoxy resins that can be employed with our curing agents in a one package system can be either solid or liquid at room temperature, the form of the resin dictating the method of incorporating the agent into the resin. The lower molecular weight resins are typically viscous liquids at room temperatures of 70–78° F. When incorporated into such liquids, the agent may be dispersed into the liquid either by conventional milling or stirring procedures. When incorporated in a solid resin, the curing agent can be incorporated by use of conventional milling process, such as a 3-roll mill.

Suitable resins include 3,4-epoxycyclohexylmethyl-(3,4-epoxy) cyclohexanecarboxylate (ERL 4221 by Union Carbide or Araldite CY 179 by CIBA Geigy), bis (3,4-epoxy-6-methylcyclohexylmethyl) adipate (ERL 4289 by Union Carbide or CY 178 by Ciba), vinylcyclohexenedioxide (ERL 4206 by Union Carbide), bis (2,3-epoxycyclopentyl) ether 4205 by Carbide); glycidyl ethers of polyphenol epoxy resins such as liquid or solid bisphenol A diglycidyl ether epoxy resins (Epon 828, Epon 826, Epon 1001 and Epon 1002 by Shell and DER 331, DER 332 by Dow Chemical Co.), tetraglycidyl methylenedianiline (TGMDA) (MY720 by Ciba), tris (hydroxyphenyl) methane based epoxy resins (XD-7142.002 experimental epoxy resin by Dow Chemical Co.); flame retardant epoxy resins such as halogen containing bisphenol A diglycidyl ether epoxy resins (DER 542, DER 511 by Dow); phenol-formaldehyde Novolac polyglycidyl ether epoxy resins (such as DEN 438, 431 by Dow), diglycidyl hexahydrophthalate (Araldite CY 183 by Ciba and Ed-5662 by Celanese). Other cycloaliphatic epoxies (such as Araldite CY 179 and CY 192 by Ciba, ERL 4090, 4205 by Union Carbide), 2-(3,4-epoxy) cyclohexyl-5,5-spiro (3,4-epoxy)-cyclohexane-m-dioxane, (CY 175 by Ciba, ERL 4234 by Union Carbide).

The epoxy resin system of this invention may further include conventional fillers and additives such as pigments and colorants. Fillers may be generally used to increase performance at high temperatures, reduce the coefficient of thermal expansion, increase thermal conductivity, decrease shrinkage (by reducing peak exotherm temperature) and alter moisture resistance. Suitable fillers include calcium carbonate, talc, aluminum oxide, flint powder, silica, mica and metallic powders (Al, Zn, etc.), calcium sulfate, glass, and the like.

Common pigments that may be used include titanium dioxide, carbon black, cadmium red, barium sulfate, antimony oxide, phthalocyanine blues and greens; red, yellow, black, and brown iron oxides; chrome oxide green, etc. Sufficient pigmentation is used to provide an opaque or colored film as needed for the desired appearance.

Leveling agents commonly used in epoxy coatings can be used as desired. For example, various leveling agents which can be used to enhance the flow of the epoxy under curing conditions are polymeric or monomeric acetals such as polyvinylformal, polyvinylacetal, diethyl-2-ethyl hexanol acetal, di-2-ethylhexyl acetaldehyde-acetal; and polyglycols and polyglycol ethers such as polyethylene glycol, polypropylene glycol, and the like.

PREFERRED EMBODIMENTS

The following examples illustrate without limiting the invention.

EXAMPLE 1

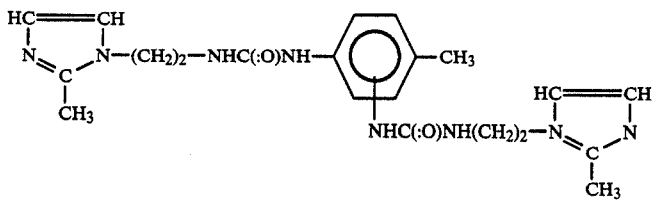

(Herein, when toluene diisocyanate is used as a reactant, it is a commercially available mixture of the 2,4-diisocyanate (80%) and the 2,6-diisocyanate (20%). Other isomers are possible. The valences may therefore appear as dangling, i.e.,

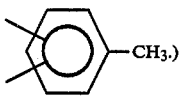

With vigorous stirring, 35 g of toluenediisocyanate was added dropwise to an aqueous solution containing 55 g of 1-aminoethyl-2-methyl imidazole and 100 ml of water. After the completion of addition, the solution was stirred further for 2 hours. A white precipitate of the above product was formed. It was filtered, washed with water, and dried at room temperature, after which it was pulverized to a fine powder.

EXAMPLE 2

Use of Product of Example 1 as Curing Accelerator

The compound (3.4 parts by weight) from Example 1 was uniformly blended with an epoxy resin containing 100 parts of an epoxy resin made from diglycidyl ether and Bisphenol A (available commercially as Epon 828 from Shell Chemical Company) and 6 parts of dicyandiamide to form a one-package epoxy system. The blend was stored in an oven at 40° C. for 10 days. No noticeable viscosity change was observed. The fresh one-package epoxy system was curable at 170° C. in 6 seconds.

EXAMPLE 3

Use in Epoxy-Anhydride System

The compound (1.5 parts) from Example 1 was mixed with an epoxy resin mixture containing 32.5 parts of Epon 828 and, as curing agent, 17.5 parts of a copolymer of styrene and maleic anhydride. The mixture cured at 170° C. in 5 seconds. At 40° C. the mixture was stable for over a month.

EXAMPLE 4

Use in Epoxy Resin

Epon 828 (19 parts) was well mixed with 11 parts of the compound from Example 1 at room temperature. No dicyandiamide was added. This mixture exhibited a fast curing at 170° C. in 5 seconds.

EXAMPLE 5

1-Aminopropyl-2-ethyl-4-methyl Imidazole/Toluenediisocyanate Reaction Product

The process of Example 1 was followed except that the imidazole reactant was 1-aminopropyl-2-ethyl-4-methyl imidazole. The corresponding bis-urea reaction product was obtained as a white powder. It was used to cure an epoxy resin with good results, following the procedure of Example 3. It showed excellent storage stability, i.e., in an epoxy resin system for over a month at 40° C..

The amount of our accelerator is not critical. A workable range is 0.01 to 20 weight %, preferably 0.01 to 5%, based on the weight of the epoxy resin.

Our accelerators provide curing temperatures suitably over the range 130°–220° C., at times ranging from about 5 seconds to one hour.

Studies of the mechanism of imidazole-curing of epoxy resins include Ricciardi et al., Mechanism of Imidazole Catalysis in the Curing of Epoxy Resins, J. Polymer Sci.: Polym. Let. Ed., Vol. 20, 127–133 (1982); and Ricciardi et al., Mechanism of Imidazole Catalysis in the Curing of Epoxy Resins, J. Polymer Sci.: Polym. Chem. Ed., Vol. 21, 1475–1490 (1983). It appears that the imidazoles are regenerated during the curing process, indicating a true catalytic function.

Storage Stability

Storage stability extending over at least a month is virtually a necessity for most industrial bulk uses of completely formulated liquid epoxy resins. For example, large vats filled with accelerator-containing resins are used for dip-work continuously over many days, and the resin must remain fluid and un-cured during this use period. Also, spray work is often supplied from tanks containing large volumes of resin, and it is essential that the resin not destabilize during use continuing over several weeks. Our new accelerators qualify eminently in this regard.

1-Aminoethylimidazoles

We used 1-aminoethyl-2-methyl-imidazole ("AMZ'), available commercially (Shikoku Company, Japan).

1-Aminopropylimidazoles

1-Aminopropylimidazoles can be prepared by hydrogenation of the corresponding source cyanoethylimidazole, thus:

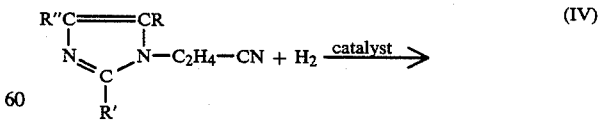 (IV)

where R, R', and R" have the meanings in (I) above.

EXAMPLE 6

1-Aminopropyl-2-ethyl-4-methyl-imidazole

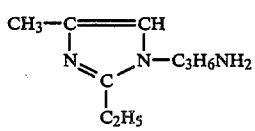

1 g 1-cyanoethyl-2-ethyl-4-methylimidazole was put in 20 ml of ethanol into a high-pressure reactor. Raney nickel (50 mg) was added as the catalyst, and the reactor was pressured to 1000 psi with hydrogen and heated to 100° C. for 18 hours. The reactor was cooled down and the excess hydrogen was vented. The product was identified as 1-aminopropyl-2-ethyl-4-methylimidazole by gas chromatography and mass spectra.

Substantially identical results were obtained when two other catalysts were used instead of Raney nickel, viz., Example 7, palladium-on-carbon; and Example 8, rhodium-on-carbon.

1-Cyanoethyl-2-ethyl-4-methyl-imidazole is available commercially and can be made by reacting 2-ethyl-4-methyl-imidazole with acrylonitrile.

For preparation of 1-aminoalkyl imidazoles generally see Chem. Abs. 93: 1145 W, citing U.K. patent application 2,016,452 of 1978 to Iizuka et al.; and Chem. Abs. 102: 132036a, citing Ger. Offen DE 3,406,414 of 1984, T. Wright et al.

We claim:

1. A single package epoxy resin composition comprising a curable epoxy resin and composition of the formula $X_mY$ where X is

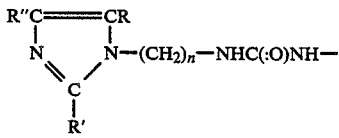

wherein
m has a value of at least 1;
R and R" are independently H, methyl, or ethyl; n is 2-5;
R' is methyl or ethyl; and
Y has a valence m and is an organic radical.

2. Resin composition according to claim 2 in which m is 2.

3. Resin composition according to claim 2 in which Y is

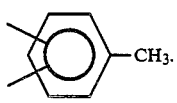

4. Resin composition according to claim 2 in which R and R" are H, n is 2, R' is methyl.

5. Resin composition according to claim 2 in which R is H, n is 3, R' is ethyl, and R" is methyl.

6. Process for making a cured epoxy resin comprising heating the epoxy resin composition of claim 1 to a temperature sufficient to cure the same.

7. Process according to claim 6 in which m is 2.

8. Process according to claim 7 in which Y is

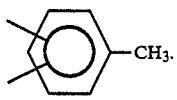

9. Process according to claim 6 in which R and R" are H, n is 2, and R' is methyl.

10. Process according to claim 6 in which R is H, n is 3, R' is ethyl, and R' is methyl.

11. Process according to claim 6 in which the epoxy resin composition comprises the reaction product of a diglycidyl ether of a polyphenol and bisphenol A.

12. Cured epoxy resin prepared by heat-curing a single package epoxy resin composition, said composition comprising an epoxy resin and a composition of the formula of claim 1.

13. Cured epoxy resin according to claim 12 in which m is 2.

14. Cured epoxy resin according to claim 13 in which Y is

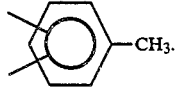

15. Cured epoxy resin according to claim 12 in which R and R" are H, n is 2, and R' is methyl.

16. Cured epoxy resin according to claim 12 in which R is H, n is 3, R' is ethyl, and R" is methyl.

* * * * *